(12) United States Patent
Menzies et al.

(10) Patent No.: US 12,111,005 B2
(45) Date of Patent: Oct. 8, 2024

(54) INFLATABLE STENT

(71) Applicant: Air Bag Stopper Holdings Limited, Edinburgh (GB)

(72) Inventors: John Menzies, Broxburn (GB); David Grant, Broxburn (GB)

(73) Assignee: Air Bag Stopper Holdings Limited, Edinburgh (GB)

( * ) Notice: Subject to any disclaimer, the term of this patent is extended or adjusted under 35 U.S.C. 154(b) by 210 days.

(21) Appl. No.: 17/051,001

(22) PCT Filed: Apr. 29, 2019

(86) PCT No.: PCT/GB2019/051179
§ 371 (c)(1),
(2) Date: Oct. 27, 2020

(87) PCT Pub. No.: WO2019/207323
PCT Pub. Date: Oct. 31, 2019

(65) Prior Publication Data
US 2021/0324990 A1  Oct. 21, 2021

(30) Foreign Application Priority Data
Apr. 27, 2018 (GB) ..................................... 1806944

(51) Int. Cl.
*F16L 55/134* (2006.01)
*F16L 55/16* (2006.01)
(Continued)

(52) U.S. Cl.
CPC .......... *F16L 55/134* (2013.01); *F16L 55/1604* (2013.01); *F16L 55/1654* (2013.01); *A61F 2/94* (2013.01); *A61F 2250/0003* (2013.01)

(58) Field of Classification Search
CPC ... A61F 2250/0048; A61M 2025/1013; A61M 2025/1047; A61M 2025/1068;
(Continued)

(56) References Cited

U.S. PATENT DOCUMENTS 2,548,602 A * 4/1951 Greenburg ............ A61M 29/02
600/184
2,927,609 A * 3/1960 Vanderlans ........... F16L 55/124
220/232
(Continued)

FOREIGN PATENT DOCUMENTS

GB         1311017 A  * 3/1973 ............ F16L 55/124
GB         2428079 A    7/2005
(Continued)

OTHER PUBLICATIONS

Foreign Communication from a Related Counterpart Application, International Search Report and Written Opinion dated Aug. 9, 2019, International Application No. PCT/GB2019/051179 filed on Apr. 29, 2019.

(Continued)

*Primary Examiner* — Robert K Arundale
*Assistant Examiner* — Richard K. Durden
(74) *Attorney, Agent, or Firm* — Conley Rose, P.C.

(57) ABSTRACT

An inflatable stent for use in the repair and maintenance of pipes such as water or gas supply pipes, or for use as a medical device comprises an inflatable portion having an inner and outer membrane. When inflated, the inner and outer membranes are radially spaced apart to define an annular space there between. The inner membrane defines a passage between a first and second end and the outer membrane defines a first diameter (D1) of the stent. The inner and outer membranes are connected by a plurality of connecting members in the annular space. End caps are (Continued)

disposed on the first and second ends of the stent which connect the inner and outer membranes. The inflatable portion further comprises an inflatable pipe or lumen engaging portion that defines a second, larger diameter (D2) of the stent, when inflated.

23 Claims, 10 Drawing Sheets

(51) Int. Cl.
*F16L 55/165* (2006.01)
*A61F 2/94* (2013.01)

(58) Field of Classification Search
CPC .. A61M 2025/1072; A61M 2025/1084; A61M 2025/1097; A61M 25/1006; A61M 25/1011; F16L 55/12; F16L 55/128; F16L 55/134; F16L 55/1604; F16L 55/16455; F16L 55/1654; F16L 55/44
See application file for complete search history.

(56) References Cited

U.S. PATENT DOCUMENTS

| | | | | |
|---|---|---|---|---|
| 2,934,361 | A * | 4/1960 | Young | F16L 55/1604 285/306 |
| 4,077,080 | A * | 3/1978 | Ross | B08B 9/0553 15/104.061 |
| 4,083,384 | A * | 4/1978 | Horne | E03F 9/00 134/167 C |
| 4,141,364 | A * | 2/1979 | Schultze | A61M 16/0434 128/207.15 |
| 4,144,908 | A * | 3/1979 | Dunn | F16L 55/134 138/93 |
| 4,582,551 | A * | 4/1986 | Parkes | F16L 55/18 264/36.16 |
| 4,646,787 | A * | 3/1987 | Rush | G01M 3/005 73/866.5 |
| 5,427,153 | A | 6/1995 | Tash | |
| 5,599,307 | A | 2/1997 | Bacher et al. | |
| 6,936,057 | B1 * | 8/2005 | Nobles | A61B 17/12045 623/1.25 |
| 6,959,734 | B2 * | 11/2005 | Lundman | F16L 55/134 137/240 |
| 7,296,597 | B1 * | 11/2007 | Freyer | E21B 33/1208 138/93 |
| 7,329,236 | B2 * | 2/2008 | Kesten | A61M 25/1002 604/96.01 |
| 8,932,326 | B2 * | 1/2015 | Riina | A61M 29/02 604/509 |
| 9,179,921 | B1 | 11/2015 | Morris | |
| 2002/0033554 | A1 | 3/2002 | Heagy et al. | |
| 2003/0066844 | A1 | 2/2003 | Boal | |
| 2012/0109179 | A1 * | 5/2012 | Murphy | A61M 25/104 606/200 |
| 2013/0103135 | A1 | 4/2013 | Vinluan | |
| 2013/0282097 | A1 * | 10/2013 | Burton | A61F 2/958 264/573 |
| 2017/0009929 | A1 * | 1/2017 | Acker | F16L 55/1612 |
| 2017/0281140 | A1 * | 10/2017 | Arahira | A61B 1/3137 |
| 2019/0366059 | A1 * | 12/2019 | Raijman | A61M 29/02 |

FOREIGN PATENT DOCUMENTS

| | | |
|---|---|---|
| GB | 2439401 A | 12/2007 |
| KR | 20100017046 A | 2/2010 |
| WO | 2019207323 A1 | 10/2019 |

OTHER PUBLICATIONS

Foreign Communication from a Related Counterpart Application, United Kingdom Search Report and Written Opinion dated Oct. 29, 2018, United Kingdom Application No. 1806944.3 filed on Apr. 27, 2018.
Foreign Communication from a Related Counterpart Application, International Preliminary Report on Patentability dated Nov. 5, 2020, International Application No. PCT/GB2019/051179 filed on Apr. 29, 2019.

* cited by examiner

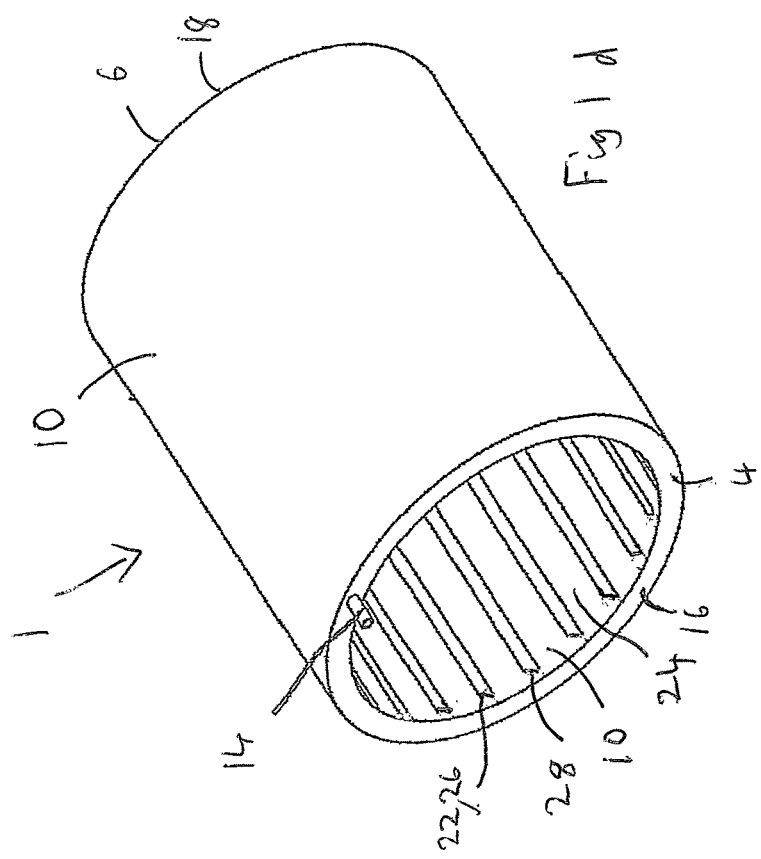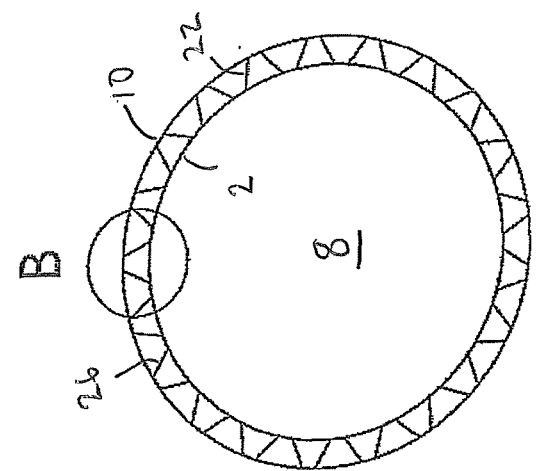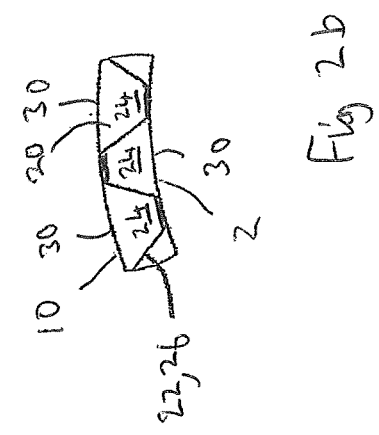

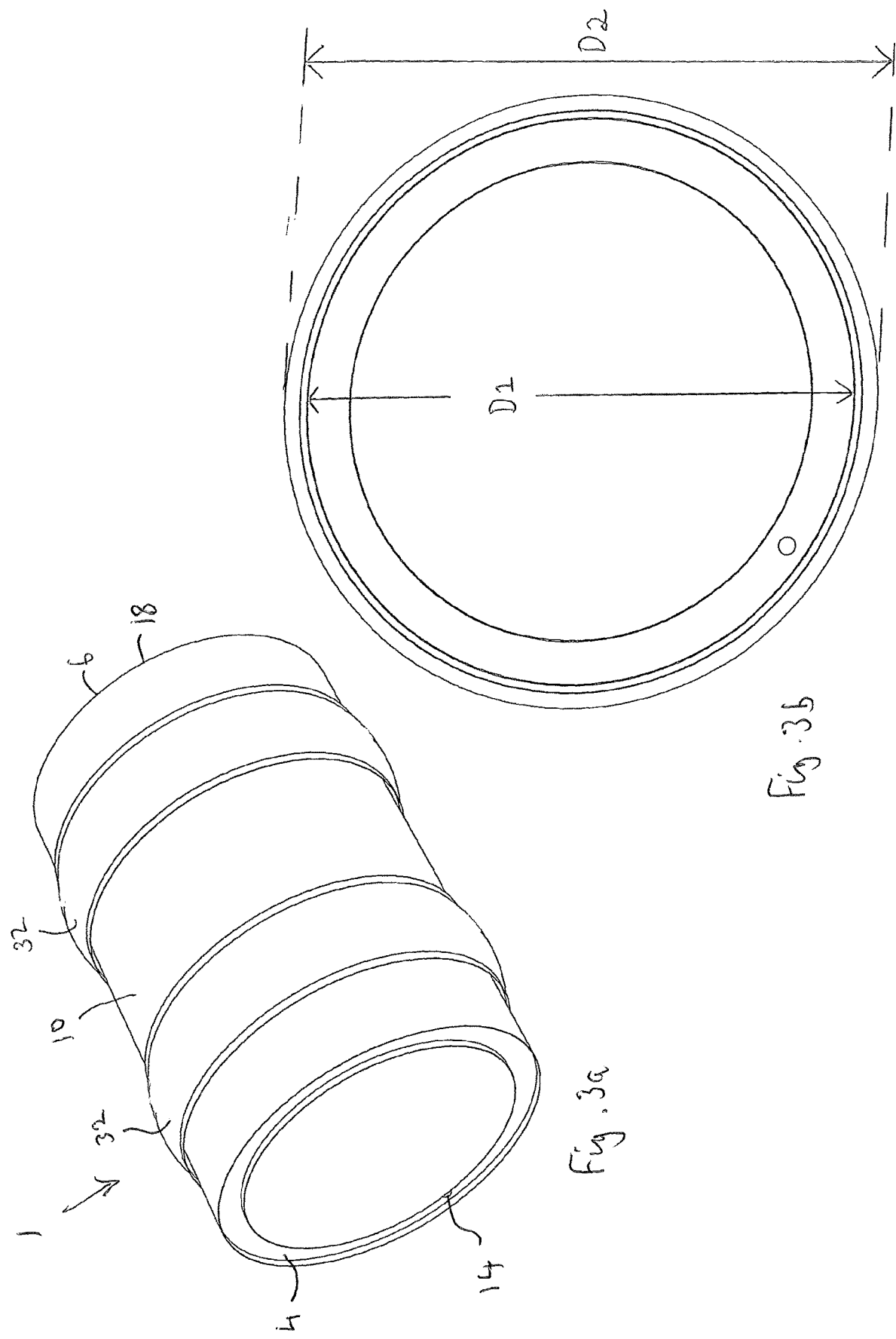

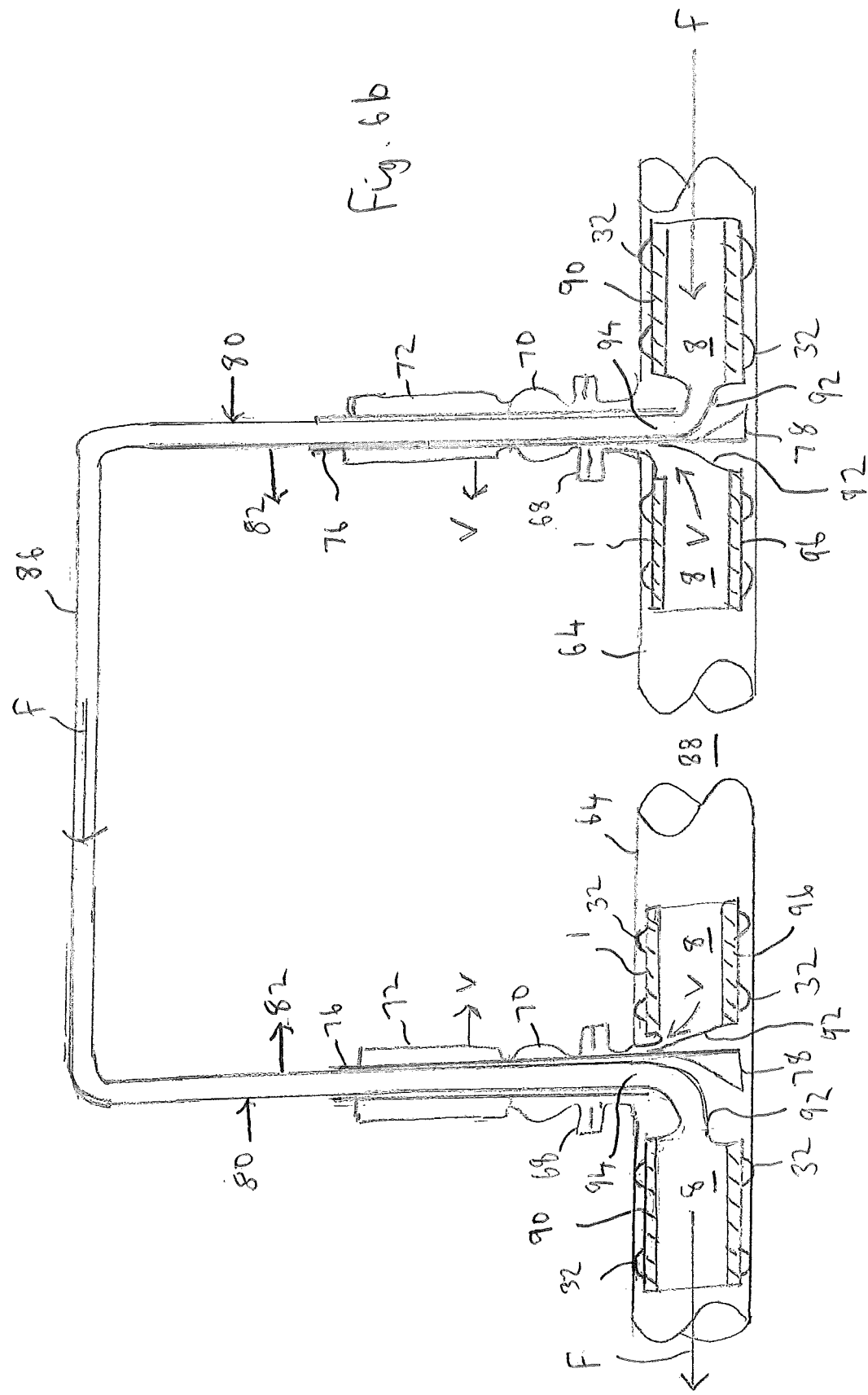

INFLATABLE STENT

CROSS-REFERENCE TO RELATED APPLICATIONS

The present application is a filing under 35 U.S.C. 371 as the National Stage of International Application No. PCT/GB2019/051179, filed Apr. 29, 2019, entitled "Inflatable Stent," which claims priority to United Kingdom Application No. 1806944.3 filed with the Intellectual Property Office of the United Kingdom on Apr. 27, 2018, both of which are incorporated herein by reference in their entirety for all purposes.

FIELD OF THE INVENTION

The invention relates to inflatable stents for use in the repair and maintenance of pipes such as water or gas supply pipes. The inflatable stents can also find use as medical devices, for example to allow maintenance of fluid flow in a damaged lumen of the body, such as the oesophagus.

BACKGROUND TO THE INVENTION

Inflatable devices such as inflatable bags have found use in stopping flow in pipes such as gas or water pipes, to allow repair and maintenance procedures to be carried out.

For example two such inflatables can allow isolation of a short section of damaged pipe, with one inflatable bag to either side of the damaged section. This avoids having to depressurise, isolate or even drain a long section of pipe to allow safe access for repair or replacement. For further example long sections of pipework can be isolated, 500 m or more, by using inflatable bags. This can be done where replacement or abandonment of an extensive system, such as a gas main, is being undertaken.

In some procedures an isolated section of pipe can be bypassed to allow flow to continue via a bypass loop of pipe that connects to either end of the isolated section. The isolated section of pipe may then be depressurised and work undertaken.

As an alternative approach, use of a stent may be considered when repairing, maintaining or remediating pipework. A stent generally has a passage through to allow flow to continue, whilst at the same time supporting or even isolating a section of pipe that is damaged; weakened or even has failed, causing leakage. Thus stent can bridge across a damaged length of a pipe (from the inside); from an undamaged section, past the damage, to an undamaged section on the other side; to provide a safe passage through for a fluid flow, even a pressurised fluid flow.

Stent operations can include isolation of damaged or failed lengths of a pipe system; sealing of leakage at pipe joints or damaged pipe walls; maintenance, repair or replacement of pipe components such as valves or pipe sections; and temporary or permanent repair of damaged pipe walls.

There is a need for improved stents and systems for use. In particular, to allow the use of an inflatable stent in relatively harsh environments such as in gas, oil and water systems, including at high pressure, for example mains water pipe systems.

Similarly there is a need for improved stents and systems of use in medical applications, where speed, ease of use and confidence of successful deployment are of great importance.

DESCRIPTION OF THE INVENTION

The present invention provides an inflatable stent comprising an inflatable portion that comprises:
- an inner membrane of a flexible sheet material defining a first end and a second end of the inflatable portion, and a passage there between when inflated; and
- an outer membrane of a flexible sheet material disposed about the inner membrane, the outer membrane defining a first diameter of the stent when inflated;
  - wherein, when inflated, the inner and outer membranes are radially spaced apart to define an annular space there between;
  - the inner and outer membranes are connected by a plurality of connecting members in the annular space, and by first and second end caps that connect the membranes at the respective first and second ends of the inner membrane; and
  - wherein the inflatable portion is further provided with at least one inflatable pipe or lumen engaging portion that defines a second, larger diameter of the stent, when the inflatable portion is inflated.

The pipe or lumen engaging portion may be a portion, for example a ring, of a resiliently flexible material. For example, of a foam, a rubber or a gel (that may be provided in a bag) or combinations thereof. Advantageously the pipe or lumen engaging portions are inflatable. Typically they are inflatable and of a flexible sheet material.

In the description of the invention described herein the term lumen is employed for the inside space of a generally tubular structure within the human or animal body. The term pipe refers to any other type of generally tubular conduit.

The inflatable portion may be provided with a plurality of the inflatable pipe or lumen engaging portions.

The inner and outer membranes are formed of a flexible sheet material. The end caps are also typically of a flexible sheet material to aid in providing a stent that (when in the collapsed state) can be compact and readily manoeuvred into position through a route that may be convoluted. The stent can then be inflated. In use the stent may be deployed along a pipe that is under pressure, for example a water mains pipe. Such a deployment may be carried out by using equipment of the known types for deployment of conventional inflatable bags into an under pressure pipe system. Thus the stent may be deployed into a pipe system via existing access points such as a branch including a valve, or by means of system specifically designed for access (and typically also egress) into an under pressure pipe system. For example, a system whereby access to a pipe is obtained by fitting a saddle and a pressure containing fitment to the pipe. The saddle and fitment allow cutting into the pipe whilst holding in the pressure. The stent is then deployed via the pressure containing fitment.

The passage may be generally cylindrical in form, having a generally cylindrical inner membrane defining it, when the stent is inflated, Other forms of passage may be provided, for example generally frusta conical, with a narrower diameter at one of the ends than at the other. Typically the inner and the outer membrane are both generally cylindrical in form when inflated. However, other shapes of inner and/or outer membrane structure may be employed. For example if a pipe is of a square cross section then an outer membrane that takes a square or substantially square form when inflated can find use. The inner membrane may take the same general form as the outer, or it may be different. The inflatable portion may take the form of a bend (when inflated) for some applications. This may allow better sealing to the inner walls of a pipe or lumen, when the stent is deployed in a curved section of pipe or lumen.

The inner membrane defines first and second ends of the inflatable portion. The outer membrane is disposed about the inner membrane and so may have corresponding first and second ends i.e, may have substantially the same, or the same, length. For example when inflated the inner and outer membranes and the first and second end caps may take the form of a cylindrical or substantially cylindrical pipe with end faces defined by the end caps. The end caps may provide flat or substantially flat end faces to the inflatable portion. Alternatively the end caps may be profiled, having a shape that projects outwardly, in generally the axial direction, from the first and second ends. For example an end cap, when viewed in cross section may present an outwards projecting curved surface towards the direction of flow. This surface may aid in reducing the turbulence and/or pressure experienced by the inflatable portion in use, avoiding the stent being dislodges due to pressure of fluid flow through it.

The connecting members may be a plurality of cords or wires that may each extend outwards from the inner membrane to the outer membrane when the stent is inflated, (a so called "dropped thread" arrangement).

The connecting members may be membrane portions (sheet portions), that may be of a flexible sheet material. The connecting member membrane portions may each extend outwards (typically radially outwards) from the inner membrane to the outer membrane and run along the axial length of the inflatable portion of the stent, i.e. in the direction from the first to the second end. Connecting membrane portions may run axially along substantially the whole length, or along the whole length of the inner membrane. Optionally there may be a gap or gaps dividing a connecting member portion that runs axially along substantially the whole length, or along the whole length of the inner membrane into sub portions. Connecting membranes running along the length of the inner membrane may be continuous, or they may be interrupted, for example by an aperture that allows fluid communication between.

Such membrane portions may divide the annular space into a series of axially extending cells around its circumference.

As an alternative membrane portions may extend outwards (typically radially outwards) from the inner membrane to the outer membrane, but run circumferentially around the annular space, between inner and outer membrane. A plurality of such membranes may be provided, one after the other along the axial length of the inflatable portion. This divides the annular space into a series of circumferentially extending cells, one after another along the axial length.

The cells may all be in fluid communication with each other. Alternatively, a selected group of cells may be in fluid communication with each other and another selected group of cells may be separately in communication one with each other. One or more cells or groups of cells may be selectively inflatable.

For example, where the membrane portions divide the annular space into a series of axially extending cells around its circumference, every second cell around the circumference of the annular space may be in fluid communication with each other and the remaining cells in fluid communication with each other but not with the second cells. This provides two groups of cells. It is then possible to inflate one group of cells without inflating the other. This can be useful, when it is desired to partially inflate the stent to provide it with some shape and/or rigidity to aid deployment along a path before fully inflating in use.

The cells may be sealed one from the other, except where fluid communication is provided.

Fluid communication between cells may be provided in a number of ways. In general openings or passageways may be provided between cells. On inflation communicating parts of the stent will be inflated by the same inflating action.

At least one end cap may define a circumferential space at an end of the stent that is in fluid communication with all of the cells. This can allow inflation of the annular space from one port that supplies inflating fluid (gas or liquid). The port for inflating may be in the end cap.

When membrane portions are employed to divide the annular space into a series of axially extending cells around its circumference they may each be a separate, typically rectangular, portion of flexible sheet material, bonding to the inner and outer membranes. Alternatively, a number of the membrane portions or all of the membrane portions may be made from a single sheet of flexible sheet material connecting alternately along the axial length of the inner membrane and then along the axial length of the outer membrane in a zig-zag arrangement dividing the annular space into axially extending cells.

With such a zig zag arrangement the cells, when viewed from an end of the stent may be generally triangular in form (cross section). Alternatively, cells may be formed to have a generally trapezoidal form. This can be achieved if the single sheet is bonded circumferentially along a portion of the inner membrane before extending radially to the outer membrane where again it is bonded circumferentially along a portion before returning to the inner membrane, and so on. This is illustrated hereafter with reference to a particular embodiment.

The use of a plurality of connecting members between the inner and outer membranes can provide relative rigidity to the inflated inflatable portion of stent as the inner and outer membranes are constrained in a fixed relationship, following inflation, avoiding or at least reducing bulging or 'ballooning' of the flexible sheet material of the inner and outer membranes. Where the connecting members are membrane portions that divide the annular space into a series of axially extending cells around its circumference, a notably stiff arrangement can be provided. For example sufficiently rigid to deal with the forces applied when a substantial flow rate of water or other fluid runs through the passage in use of the stent. Where the connecting members divide the annular space into a series of circumferentially extending cells similar benefits in stiffness may be contemplated.

The inflatable portion of the stent is further provided with at least one or a plurality of pipe or lumen engaging portions of flexible sheet material that define a second, larger, diameter of the stent, when inflated. Typically the pipe or lumen engaging portion or portions provide the second diameter along only a part or parts of the length of the inflatable portion. These inflatable pipe or lumen engaging portions allow the stent to be installed in pipes or lumens of differing diameter (larger than the first diameter) and yet still firmly engage with the pipe or lumen walls. The engagement can provide a seal with the pipe or lumen walls. At the same time the inner and outer membrane arrangement can be fully inflated, to achieve the relatively rigid structure of the inner and outer membranes connected by the end caps and the connecting members. The passage between the first end and the second end, defined by the inner membrane is relatively rigid and robust for use e.g. where a turbulent and/or solids containing flow through of a fluid is anticipated in use of the stent.

A yet further advantage of the plurality of pipe or lumen engaging portions is that, when the stent is employed in a pipe or lumen of larger diameter than the first diameter, an external annular space may be defined between the inside of the pipe or lumen, the pipe or lumen engaging portions, and the outer surface of the outer membrane.

This external annular space can be accessed, for example to obtain samples, to allow in situ pressure testing or control, to view the interior surface of the pipe or lumen (e.g. by a camera or a fibre optic cable directing light to a camera), or even to allow repair of the pipe or lumen (e.g. by injection of a filler material that sets). To that end the stent may be provided with a port providing fluid communication from the passage through the annular space and out of the outer membrane, at a location between pipe or lumen engaging portions.

Furthermore when the stent is installed in a section of pipe or lumen that is damaged, contact between the outer membrane and the damaged part of the pipe or lumen wall may be avoided, reducing the risk of further damage being caused on inflation of the stent.

Pipe or lumen engaging portions may be provided one at (or near) each end of the inflatable portion of the stent, Pipe or lumen engaging portions may be provided at other locations along the length of the inflatable portion of the stent. Additional portions, for example one or several, at intervals along the length of the stent, may provide more secure engagement to pipe or lumen walls. The arrangement may aid in gripping the pipe or lumen wall, and/or providing more effective sealing to prevent fluid flow past the stent (between the stent and the pipe or lumen wall).

The pipe or lumen engaging portions may be provided in various ways. The pipe or lumen engaging portions may be larger diameter (when inflated) parts of the outer membrane. They may be larger diameter parts of the outer membrane that connect to the respective end cap.

The pipe or lumen engaging portions may be formed as separate chambers which may be separately inflatable or may be in fluid communication with the annular space and inflate when the annular space, or a part of the annular space, (such as a cell formed by the connecting members and inner and outer membranes), is inflated.

More generally inflation of the inflatable portion of the stent occurs when the annular space is filled with an inflating fluid and the pipe or lumen engaging portions are also inflated with an inflating fluid. The inflating fluid may be a gas (e.g. air or a non-flammable gas such as nitrogen), a liquid (such as water), a fluid that sets as a solid (such as a curable resin composition) or even a foam, such as a foam composition that sets as a solid foam. The inflating fluid may be supplied to different inflatable parts of the stent via appropriate ports or manifolds. Conveniently and as discussed above, different parts of the inflatable portion of the stent are in fluid communication (have apertures or passageways connecting between) so as to reduce the number of locations where inflating fluid is applied to inflate the stent as a whole.

As the stent is typically deployed along a pipe or a lumen before inflation, it is convenient for the stent to be inflatable by supplying inflating fluid from only one end. For example, by having an inflation port or ports, or an inflation manifold or manifolds, for feeding inflating fluid into the inflatable portion on one of the end caps. Alternatively, port(s) or manifold(s) may be located at or near one end of the stent.

The stent has an inflatable portion. For some uses there will be a single inflatable portion, which may constitute the main body of the stent. However, as an alternative, the stent may have two inflatable portions, typically of the same form as discussed above. Each may have the same or different optional features. The two inflatable portions may connect to each other via a tubular portion of flexible sheet material, to provide flow through the stent as a whole. The tubular portion of flexible sheet material may be e.g. cylindrical but other shapes are contemplated. The tubular portion of sheet material can provide a sealing engagement between the two inflatable portions. Thus when deployed and inflated, with both inflatable portions in sealing engagement with the walls of a pipe or lumen, the stent provides a passage for through flow of fluid that extends through the first inflatable portion, the tubular portion of flexible sheet material and the second inflatable portion.

The tubular portion of flexible sheet material may be of the same type of material as the membrane sheets of the inflatable portions. However, to allow containment of pressure the tubular portion of flexible sheet material may be of a different material and/or may be reinforced; for example with a braided reinforcement or layers of reinforcement such as found in pressure hoses and the like.

Also contemplated is a stent including three or even more inflatable portions, typically with a tubular portion of flexible sheet material between each pair of inflatable portions, along the length of the stent.

Arrangements with two or more inflatable portions can have advantages. Tubular portion of membrane sheet material connecting the relatively stiff or rigid inflatable portions (when they are inflated) may more easily accommodate imperfections, and/or bends or even radial displacement between ends (following breakage) in a pipe or lumen. Relatively less material is employed where the stent is not inflatable along its whole length, which may aid in deployment through a narrow opening. The use of tubular portions of membrane sheet material can make accessing the external annular space easier as passage through only a single membrane can provide it.

Inflating fluid can be supplied by means of a suitable tube, or tubes, advantageously connecting at one end of the stent. A suitably stiff inflating tube may be employed as a deployment rod connecting to one end of the stent and enabling the uninflated stent to be moved along a path to the location where in may be inflated.

More generally the stent may be deployed by using a deployment rod. Alternatively deployment by a robotic device (tethered or untethered by umbilical) may be used. The deployment rod may generally be resiliently deformable to allow control of the stent but also to allow bending around the contours of a deployment path, such as through valves and around bends. A deployment rod is convenient when the stent is deployed into a pressurised pipe system using under pressure deployment equipment. The rod can pass through a gland in the deployment system for advancing and/or withdrawing the stent in the same manner as employed for advancing or withdrawing inflatable bags employed in prior art pipe sealing systems.

Conveniently a deployment rod for deploying the stent may pass through the passage and connect to the stent at the end distal to that of a user deploying the stent. Thus the end of the deployment rod connecting to the stent pulls rather than pushes the stent along a path e.g. along the inside of a pipe or lumen. Alternatively or additionally the deployment rod may connect to the proximal end of the stent to allow pushing of the stent on insertion along a pipe or lumen.

When withdrawing the stent a proximal connection allows the stent to be pulled from the pipe or lumen. The deployment rod may carry or may be an inflation tube for the stent. The deployment rod may include other apparatus. For example the deployment rod may mount at least one camera and optionally at least one light. This allows viewing of the path (e.g. pipe) along which the stent is being deployed. Conveniently where a camera or camera and light are employed they are mounted towards or at an end of the deployment rod, forwards of the end of the stent. Thus the camera can provide a view of the path ahead for an operator deploying the stent, Other optional equipment that may be provided with stents and may conveniently be included in or on a deployment rod includes one or more of a microphone, hydrophone, and a sonde sensor or other device to allow location of the stent from above ground/outside the pipe or lumen. The front end of a deployment rod may include a formation such as a ball or cone shape to facilitate guiding the apparatus along a pipe or lumen.

A deployment rod may be releasably detachable from the stent. For example where the rod includes or is an inflating tube, the connection to an inflation port may be via a non-return valve fitted to the port, to prevent deflation on detachment of the deployment rod. Thus a remotely detachable inflating tube and/or deployment rod combined with a self-closing valve or valves, is convenient where the stent is to be left in places for an extended period of time.

When withdrawing the stent it may be convenient for the deployment rod to connect to the proximal end of the stent (i.e, the end of the stent nearer a user who will be manipulating the deployment rod). When the stent is being withdrawn from a location (after deflation or partial deflation) this connection can allow the rod to pull the stent back out from the pipe or lumen where it has been deployed. Conveniently, (especially where making use of a deployment rod that connects to the stent at the end distal to that of a user) the proximal connection can be by one or more, (typically a plurality) of cords or straps that connect from the deployment rod to an inflatable portion of the stent. The cords or straps may connect to the outer membrane for example.

The cords or straps may extend, when the inflatable portion is inflated, from a connection point or points on the deployment rod, to the proximal end of the stent. The connection point on the deployment rod may conveniently be at a location closer to the user than the proximal end of the stent.

The inner membrane defines a passage from the first end to the second end of the inflatable portion. Typically such passages through the inflatable portions and connecting tubular membrane portions (if employed) may provide fluid communication from one end of the stent to the other, allowing flow through a pipe or lumen to continue, after installation (and inflation). This is typical for a stent used in medical applications.

Alternatively the passage through the stent can be blocked e.g. by an end cap, or a sealing membrane part way along the passage, if through flow is to be prevented in a particular use.

For example the stent may be provided with one or more sealing membranes part way along the passage. This can allow fluid flow and/or venting of the passage at one end of the stent, or at an intermediate portion of the stent, to be separated from fluid flow and/or venting at the other end of the stent. Venting or fluid flow can be out through a suitable port in the wall of the stent (inner and outer membranes).

Conveniently for some applications one end of the stent may be provided with an end that is tubular, has sealing engagement to the passage through the stent and reduces in size, to connect to; or be connectable to; a tubular. For example a generally conical end can be connected to or connectable to a pipe or hose for the passage of fluid.

At least the inner and outer membranes and the pipe or lumen engaging portions are of a flexible sheet material. They may be of polymeric or rubber type materials and may be reinforced by fibres or woven fabric. For example rubber, polyurethane, fabric (that may be rubber or polyurethane coated) may be employed. The flexible sheet material may be of different thicknesses and the flexible sheet material may include portions comprising laminated together flexible sheet materials. The flexible sheet material may be reinforced. For example, by metal wire or by plastic members of a material that is relatively stronger and/or stiffer than the flexible sheet material.

The stent may be manufactured in various ways, for example by bonding e.g. bonding with adhesive or RF welding, of plastic sheet material pieces together. Stitching may be employed to attach components one to another. Alternatively, extrusion can be used to extrude the inner and outer membrane, and membrane portions in between, as a one piece unit. The end caps and any other parts required can then be added to the extrusion. Vacuum forming, moulding, casting, or even 3D printing type methods of manufacture are also contemplated.

The present invention also provides a method of by-passing a section of pipe or a lumen, the method comprising:
obtaining access to a section of pipe at two locations, one upstream and one downstream, to either side of a section of pipe to be by-passed;
deploying an inflatable stent as described herein and having a passage there through, into each of the two locations;
inflating the stents so as to obtain substantially sealing engagement with the inner walls of the pipe;
providing a by-pass pipe running externally of the pipe from the upstream location to the downstream location; and
providing a route of fluid communication from upstream to downstream through the passages of the inflatable stents and via the by-pass pipe to by-pass the said section of pipe.

The access locations may be existing connections to the pipe such as a branch including a valve, or by means of system specifically designed for access (and typically also egress) into an under pressure pipe system.

The method may further include providing a third inflatable stent and deploying it through one of the access locations in the direction of the by-passed section of pipe. This can allow venting and or inspection of the by-passed section via a fluid communication such as a pipe that may vent, for example, via the corresponding access pipe. As an alternative third and fourth inflatable stents may be provided, one deployed through each access location, allowing venting or inspection via either or both stents and access locations.

The route of fluid communication from upstream to downstream is generally substantially sealed to avoid loss of fluid; as is usual for by-pass work. For example one end of each stent may be provided with an end that is tubular, has sealing engagement to the passage through the stent and reduces in size; and is connected to the by-pass pipe.

BRIEF DESCRIPTION OF THE DRAWINGS

FIGS. 1a to 1d show an inflatable stent and various details of its structure;

FIGS. 2a, 2b show an alternative stent structure;

FIGS. 3a to 3f show an inflatable stem fitted with pipe or lumen engaging inflatable portions;

FIG. 6b shows a pipe by-pass system making use of inflatable stents.

DESCRIPTION OF SOME EMBODIMENTS WITH REFERENCE TO THE DRAWINGS

Figure 1A:
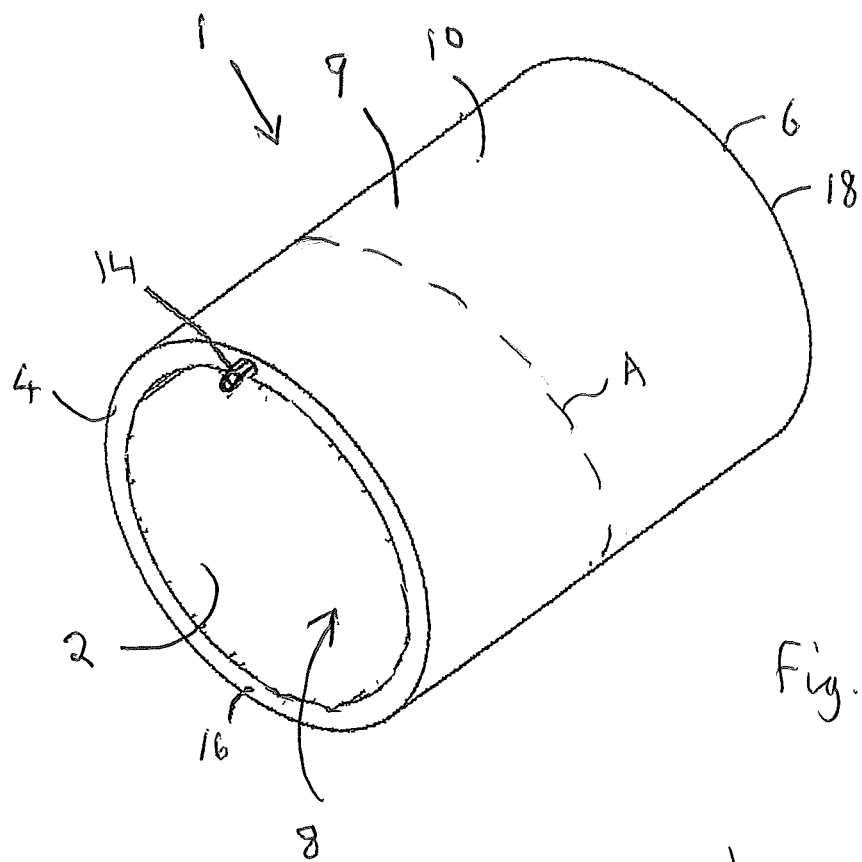

FIG. 1 shows in schematic perspective view an inflatable stent 1, without the pipe or lumen engaging portions of a stent of the invention (see FIGS. 3, 4 and 5 and the description below for these).

The stent 1 is shown in its inflated state and is cylindrical. The stent 1 has an inner membrane 2 defining first and second ends 4, 6 and a passage 8 allowing through flow of fluid. In FIGS. 1 to 4 as follows the stent has only one inflatable portion 9. FIG. 5 (discussed below) shows an alternative arrangement with two inflatable portions.

Figure 1B:
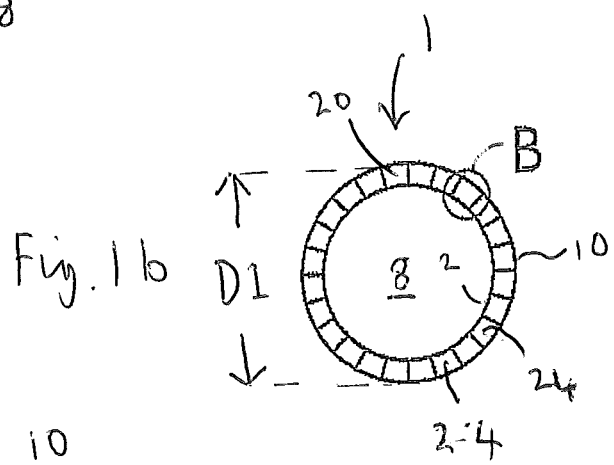
Figure 1C:
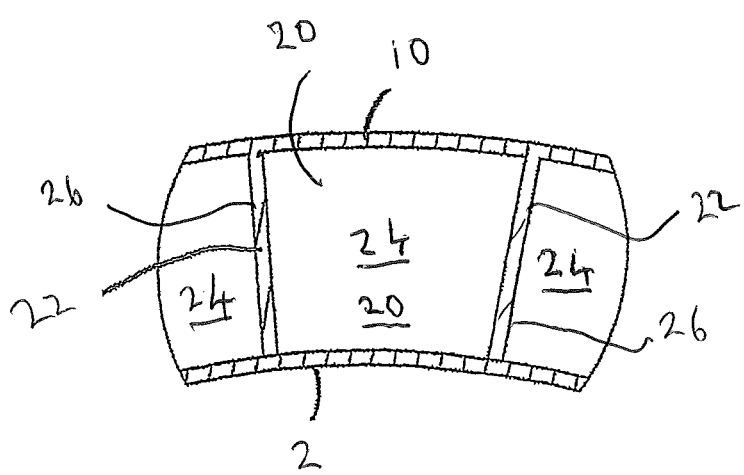

Outer membrane 10 is spaced apart from inner membrane 2 and defines a first diameter D1 of the stent (FIG. 1b). Also visible in FIG. 1a is a port or valve 14 located in in one of the end caps 16, 18 provided at either end of the stent. Port 14 has been used to inflate the stent by filling it with inflation fluid.

Cross section view FIG. 1b (at dashed line A) shows the annular space 20 between membranes 2 and 10. Annular space 20 is divided, by connecting members 22 into a series of cells 24 that are axially extending (i.e. running in the direction from the first to the second ends). These can be more clearly seen in magnified view (FIG. 1c) of part B in FIG. 1b and further in FIG. 1d as discussed below.

The connecting members 22 take the form of portions of membrane sheet ("membrane portions"). The membrane portions 26 extend from the first end 4 to or towards the second end 6. They connect the inner and outer membranes 2, 10 and are joined in sealing engagement with them. FIG. 1d shows the same perspective view as FIG. 1a but with the inner membrane absent, to allow viewing of the connecting members 22 (membrane portions 26) which take the form of rectangular portions of flexible membrane sheet that run spaced apart and parallel between the ends 4,6 in this example. The extreme ends 28 of membrane portions 26 do not extend to meet and seal to end cap 16. Thus when inflating the device through inflation port 14, all the cells 24 are in fluid communication via the space between the extreme ends 28 and the end cap 16. A similar arrangement may be provided at the other end 6 of the stent 1, which may aid in even and reproducible inflation from a deflated state.

FIG. 2a shows, in a cross section view like that of FIG. 1b, an alternative arrangement of connecting members 22. In this arrangement connecting members 22 also take the form of membrane portions 26 extending and connecting between the inner and outer membranes 2, 10. In contrast to FIG. 1c, the membrane portions 26 do not each extend along a radius. In FIG. 2a the cells 24 are generally trapezoidal in cross section but they alternate in location of the base 30 of each trapezoid around the circumference of the stent (see magnified view of part B in FIG. 2b). The arrangement in FIG. 2 may be formed by use of a single sheet of membrane material running circumferentially in a zig zag fashion in the annular space 20 with alternate bonding to the inner 2 and then the outer 10 membrane.

FIG. 3a shows in schematic perspective a stent 1 of the same general construction as those of FIG. 1 or 2 with like parts numbered the same. The stent of FIG. 3a also includes two inflatable pipe or lumen engaging portions 32. The pipe or lumen engaging portions 32 are spaced apart and attached to the outer membrane 10 they define a second, larger, diameter D2 of the stent, as indicated in end view FIG. 3b. In this example both portions 32 define the same diameter D2, In other examples where the stent may not be a regular cylinder and/or the pipe or lumen engaging portions may have different sizes, the second diameter D2 may be defined as the largest provided.

Figure 3C:
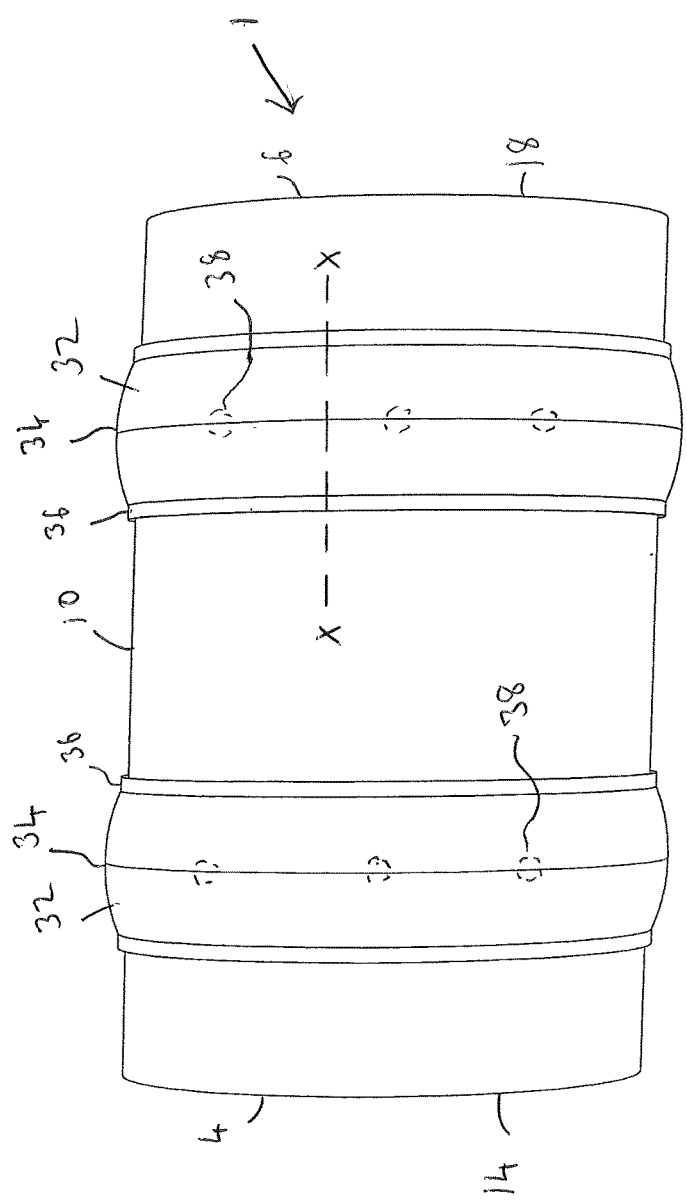
Figure 3F:
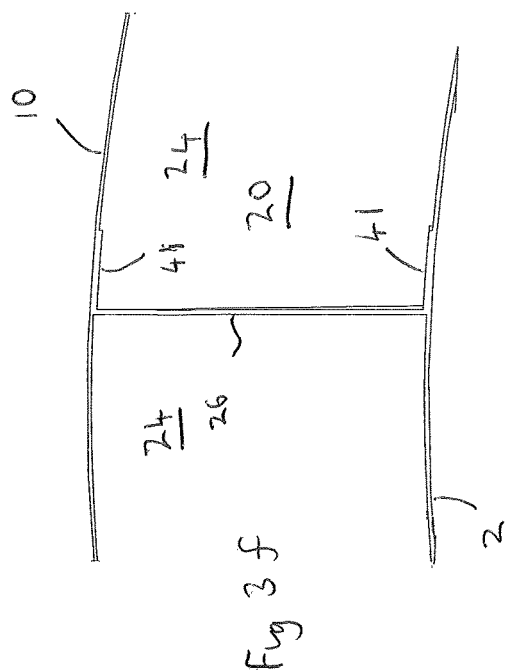

FIG. 3c shows the stent 1 of FIGS. 3a, 3b in elevation. As can be seen in this view the pipe or lumen engaging portions 32 each have a largest diameter in the middle part (indicated on the figure by centre line 34) and relatively broad edges 36 where sheet material pieces are joined together. Dashed circles indicate the location of passages 38 communicating with the annular space to allow inflation. The structure is also shown in schematic cross section FIG. 3d taken through line X-X of FIG. 3c.

Figure 3D:
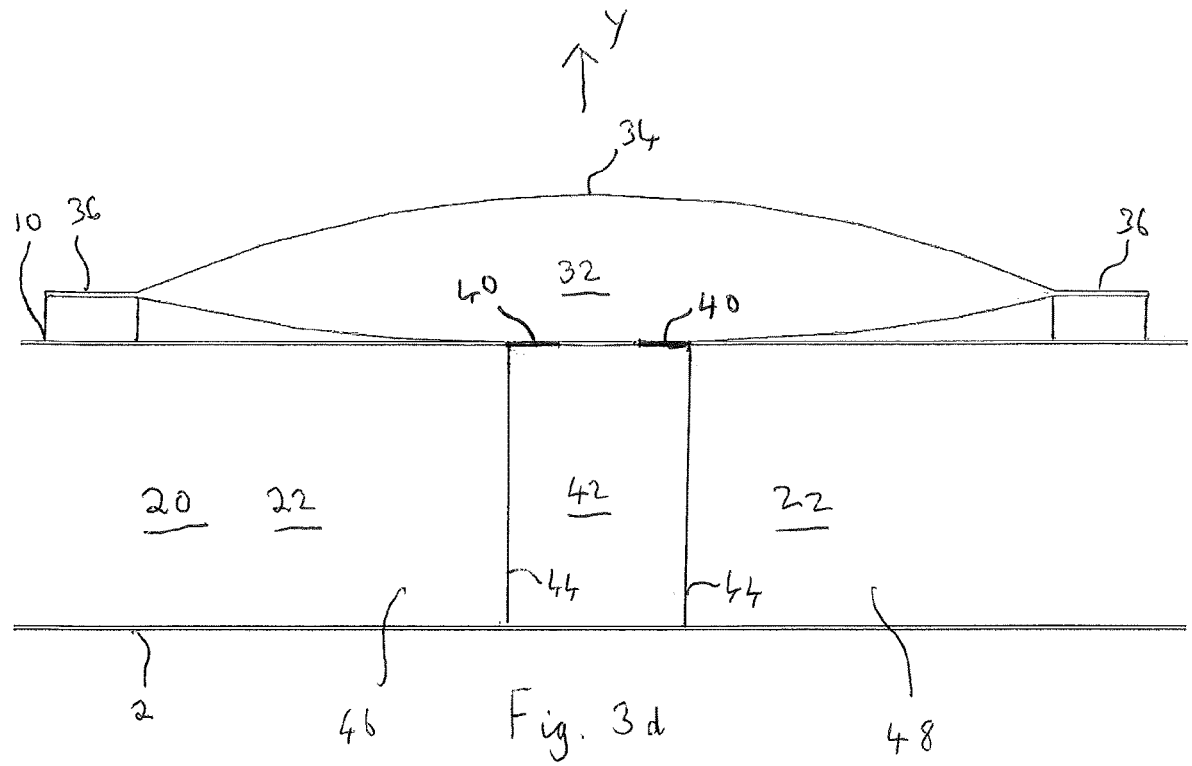

As can be seen in FIG. 3d the inflated pipe or lumen engaging portion 32 is attached to the outer membrane 10 at two regions 40 of bonding (e.g. RF welding). The two regions of bonding 40 run circumferentially around the diameter of outer membrane 10. In this example gap 42 between edges 44 of connecting member sub portions 46, 48 of connecting member membrane portion 22 allows access to make the circumferential bonds at the bonding regions 40 during the manufacturing process. Gap 42 also provides fluid communication between cells 24 (see FIG. 1c) defined by connecting members 22. In this example pipe or lumen engaging portion 32 is otherwise free from attachment to the rest of the stent and so can readily inflate radially outwards in direction Y. This may aid in making more positive (e.g. sealing) engagement with the wall of a pipe or lumen in use, for example if the pipe or lumen has some variance in diameter or is oval rather than a perfect circle in diameter.

Figure 3E:
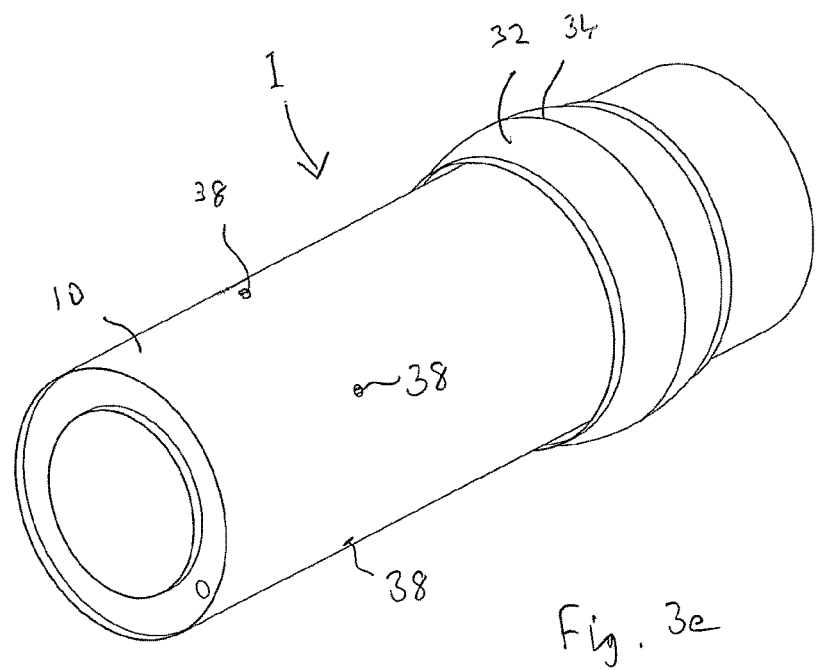

FIG. 3e shows the same stent 1 as is shown in the other FIG. 3; but with only one of the two pipe or lumen engaging portions 32 shown. This allows viewing of the passages 38 that communicate with the annular space to allow inflation of the pipe or lumen engaging portion. In this example passages 38 are spaced circumferentially about outer membrane 10 and in alignment with the largest diameter part (indicated on the figure by centre line 34) of the pipe or lumen engaging portions 32, FIG. 3f shows in a detail similar to FIGS. 1c and 2b a method of bonding membrane portions 26 to inner and outer membranes 2, 10, In this example end parts 41 of the membrane 26 illustrated are fused by RF welding to the inner and outer membranes.

Figure 4A:
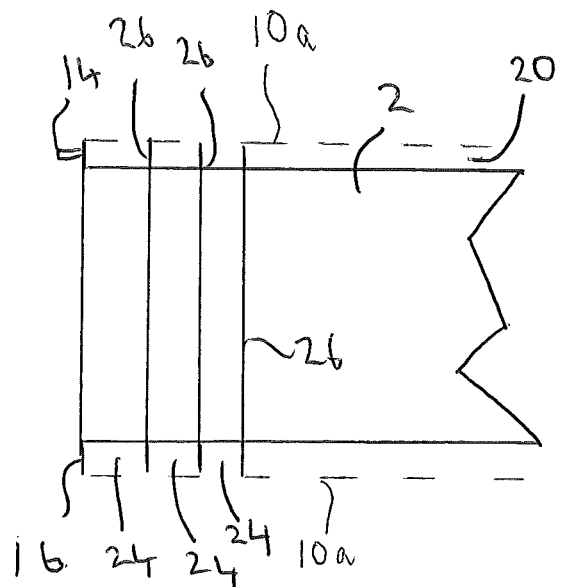
FIGS. 4a to 4c show optional features for an inflatable stent.
Figure 4B:
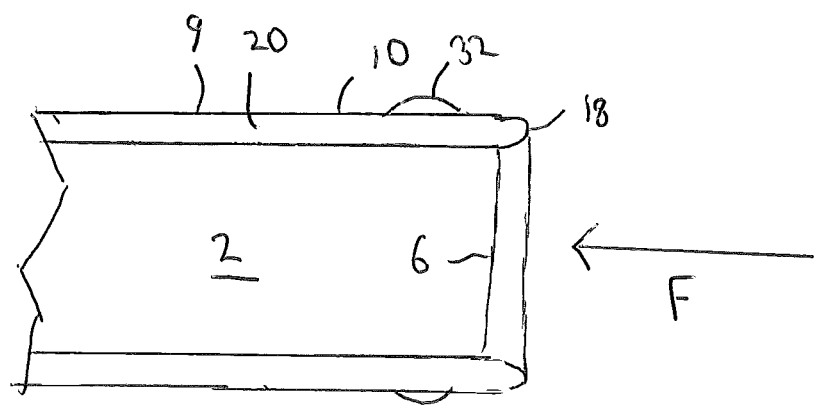
Figure 4C:
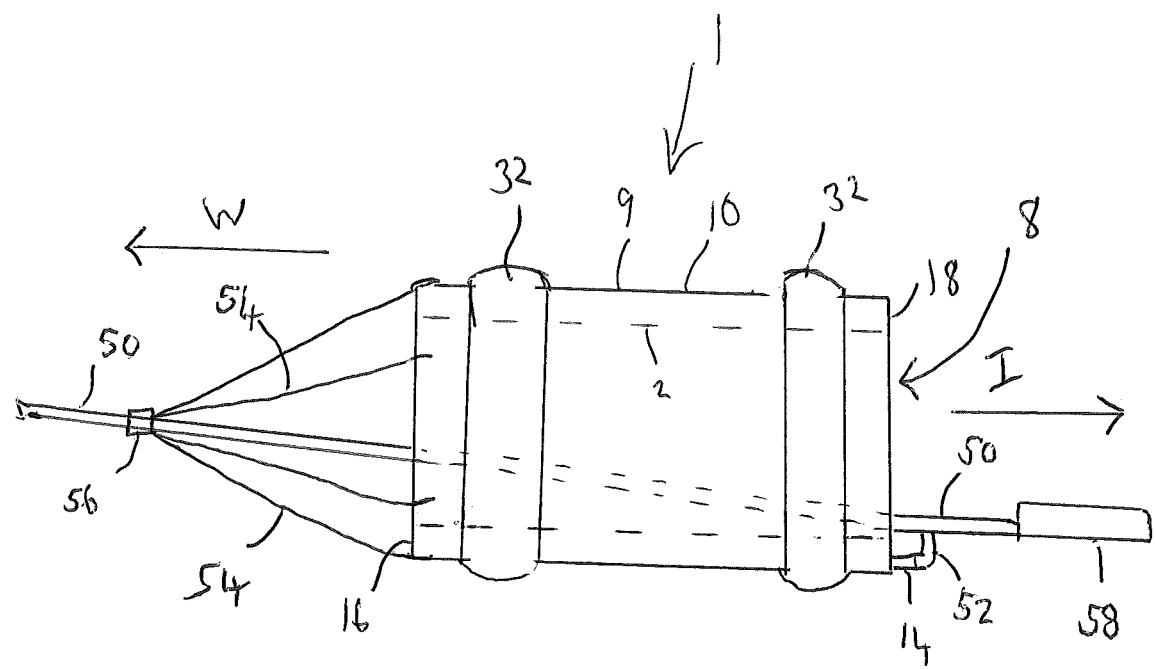

FIGS. 4a, 4b and 4c show schematically some alternative arrangements that may be employed in inflatable stents.

In FIG. 4a a part of an inflatable portion 9 of a stent 1 is shown in part elevation view with the outer membrane 10 removed (position suggested by dashed lines 10a) to allow viewing of membrane portions 26. In this example they extend circumferentially in alignment with end cap 16 to divide the annular space 20 into cells 24 that each extend circumferentially with one cell 24 after another along the length of the inflatable portion.

In FIG. 4b an inflatable portion 9 of a stent 1 is shown in partial cross-section elevation view. End cap 18 has a profile projecting from the end 6 of inner membrane 2. This may serve to reduce pressure from a fluid flow suggested by arrow F acting to displace the inflatable portion from its selected location in a pipe or lumen.

In FIG. 4c a stent 1 having an inflatable portion 9 is shown in elevation. In this example the stent 1 is fitted with a deployment rod 50 that extends through the passage 8 of inflatable portion 9. The deployment rod 50 includes within it an inflating tube 52 that emerges from the rod 50 and connects to the valve 14 at the distal end (18 in this example) of the stent 1. When the stent 1 (typically in a deflated state rather than inflated as shown in the figure) is being inserted along a pipe or lumen by pushing the rod 50 in the direction of arrow I, then the connection of the inflating tube 52 to valve 14 results in the stent being pulled into position by rod 50.

At the proximal end 16 of the stent a number of cords 54 attach to the circumference of the outer membrane 10 and to a more proximal (to a user) connection point 56 on the connecting rod, After use, when a user withdraws the stent by pulling in the direction W (typically after deflating or partially deflating) then the cords 54 allow the inflating portion 9 to be pulled from end 16 back out of the pipe or lumen.

Also included in this example is a camera and light assembly 58, which may also include other components such as gas sensors. The assembly 58 allows viewing of a pipe or lumen ahead of the stent 1.

Figure 5:
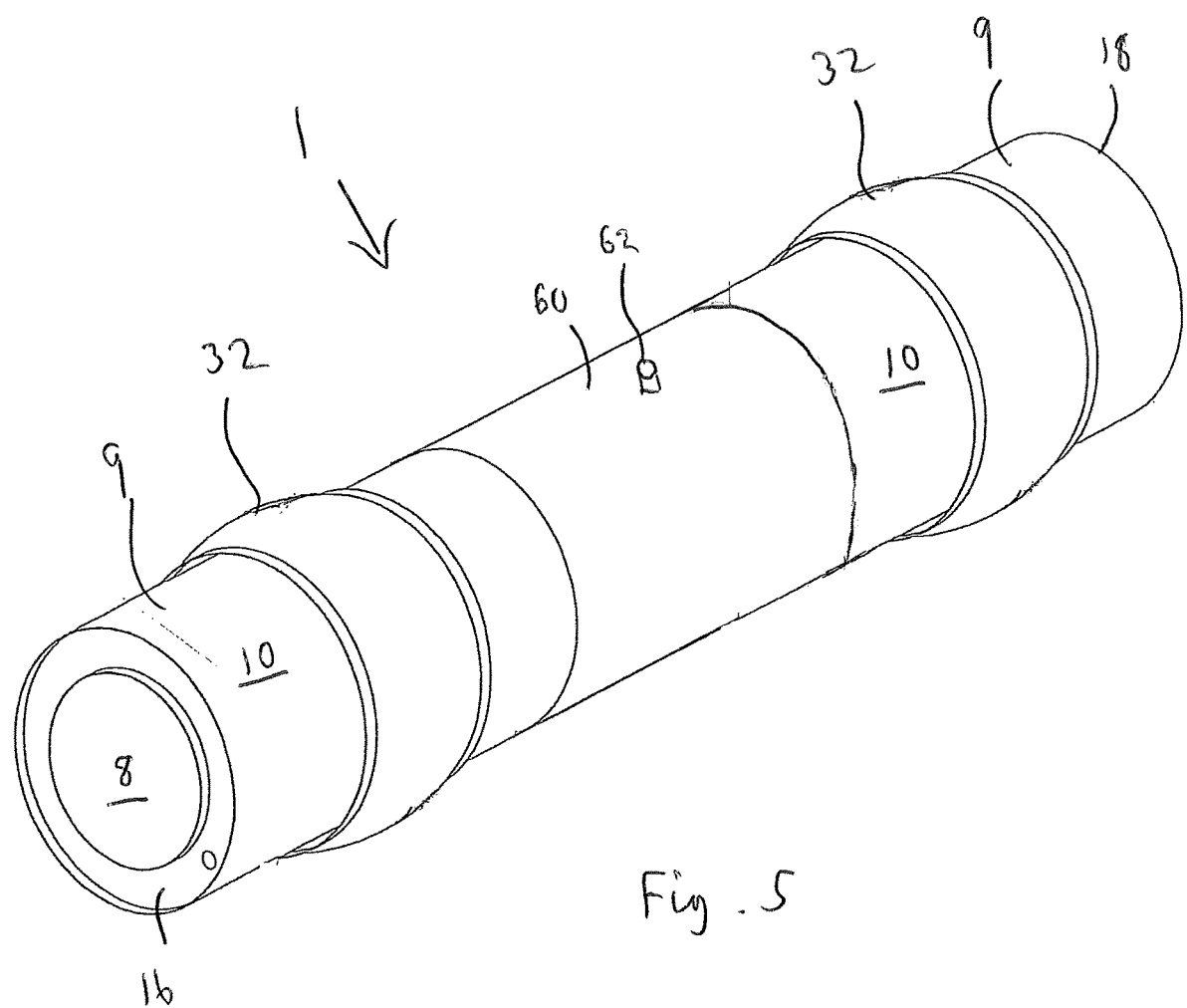
FIG. 5 shows an inflatable stent with wo inflatable portions.

FIG. 5 shows a stent 1 including two inflating portions 9 that are connected by a tube of reinforced flexible sheet material 60. The inflating portions are of the same general form as those shown in FIGS. 3, but only one inflatable pipe or lumen engaging portions 32 is provided on each portion 9. A port 62 can provide access to the passage 8, via end 16 or end 18 if required. For example; by a sensor or camera for inspection; for a delivery tube for filler material to reinforce or repair a pipe, or to allow purging and/or venting and/or monitoring of the external space between the inflatable portions 9.

Figure 6A:
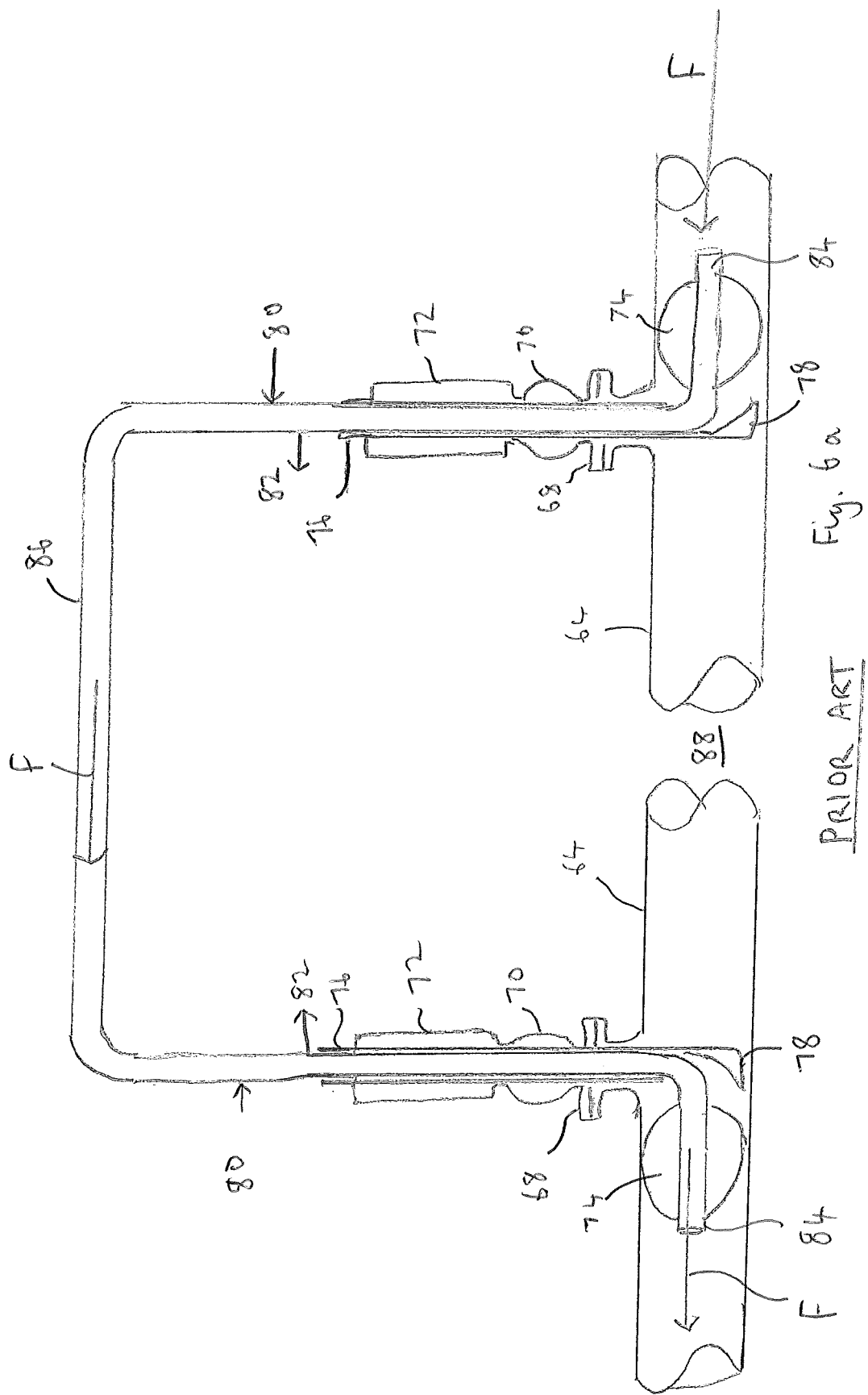
FIG. 6a shows a prior art pipe by-pass system.

FIG. 6a shows schematically a prior art arrangement for by-passing a pipe 64, such as a mains gas or water pipe. In this example access to pipe 64 has been made via flanged 'tee' connections 68 leading to hydrant valves 70, onto which an under pressure delivery system casing 72, for inflatable stopper bags 74, has been fitted. In FIG. 6a the bypass system is shown in use. Inflatable bags 74 have been inserted with the assistance of a delivery tube 76 that includes a 'nose' or stop 78 at its lower end. This nose 78 aids in delivery of the bags 74, and also, in the position shown, can aid in preventing inflating bags 74 being displaced by pressure and flow of fluid in the pipe 64.

Inflatable bags 74 have been inflated by inflating fluid delivered via ports 80 and appropriate inflating tubes (inflating tubes and other small details not shown in this schematic view). In some prior art systems the inflating fluid for bags 74 can be the fluid of the pipe 64, typically extracted at ports 82 and fed via a pump into ports 80.

Bags 74 are provided with pipes 84 that connect through casing 72 to bypass pipe 86. Thus the flow along pipe 64 is diverted via by pass pipe 86 as indicated by arrows F, to allow work to be carried out in the bypassed pipe section 88. It will be understood that the flow direction may be reversed from that shown or there may be no flow, depending on the usage of the fluid in the pipe.

FIG. 6b shows an alternative by-pass making use of inflatable stents of the invention, shown in cross-section and generally of the form shown in FIG. 3a. Two inflatable stents 90 are allowing the by-pass flow F and each has an end 92 connecting from passage 8 to give sealed fluid communication to tube 94; and hence to by-pass pipe 86. In this example the ends 92 reduce in size from the larger diameter of passage 8 to the smaller diameter of tube 94. Thus section of 88 of pipe 64, between tee connections 88 is by passed. This arrangement allows secure placement of the stents 90 in pipe 64. Passages 8 and ends 92 can aid in providing good flow through in the by-pass via tubes 94. Furthermore the stents 90 are relatively low (inflated) volume devices that can readily be inflated to higher pressures, such as are required for higher pressure pipe systems.

FIG. 6b also shows optional inflatable stents 96, shown in cross-section and generally of the form shown in FIG. 3a. Each is placed via the respective delivery system through connections 68 as used for stents 90, but in the direction of the by-passed (isolated) section 88 of pipe 64, These stents 96 include an end 92 connecting from passage 8 to allow venting along a tubing connecting through and out of casing 72 as suggested by arrows V (venting tubes and other small details not shown in this schematic view). In this example the ends 92 reduce in size from the larger diameter of passage 8 to the smaller diameter of a vent tube. The section 88 can thus be vented if desired. Inspection by camera or other sensors through stents 96 can also be contemplated. In an alternative arrangement only one stent 96 may be employed, with venting and/or inspection available from the respective side of section 88.

If required the space between a stent 90 and a stent 96 may also be vented. For example, via a tubing connecting to a port on casing 72.

The invention claimed is:

1. An inflatable stent comprising an inflatable portion that comprises:
   an inner membrane of a flexible sheet material defining a first end and a second end of the inflatable portion, and a passage there between when inflated; and
   an outer membrane of a flexible sheet material disposed about the inner membrane, the outer membrane defining a first diameter of the stent when inflated;
   wherein, when inflated, the inner and outer membranes are radially spaced apart to define an annular space there between;
   the inner and outer membranes are connected by a plurality of connecting members in the annular space, and by first and second end caps that connect the membranes at the respective first and second ends of the inflatable portion; and
   wherein the inflatable portion is further provided with at least one inflatable pipe or lumen engaging portion that defines a second, larger diameter of the stent, when the inflatable portion is inflated;
   wherein the at least one inflatable pipe or lumen engaging portion is inflatable by being in fluid communication with the annular space and inflates when the annular space, or a part of the annular space, is inflated;
   wherein the at least one inflatable pipe or lumen engaging portion is formed as a separate chamber bonded to the outer membrane; and
   wherein the at least one pipe or lumen engaging portion is otherwise free from attachment to the rest of the stent.

2. The inflatable stent of claim 1 wherein the inflatable portion of the stent is provided with a plurality of inflatable pipe or lumen engaging portions.

3. The inflatable stent of claim 2 further provided with a port providing fluid communication from the passage through the annular space and out of the outer membrane, at a location between two of the plurality of inflatable pipe or lumen engaging portions.

4. The inflatable stent of claim 1 wherein an inflatable pipe or lumen engaging portion is provided at or near each end of the inflatable portion of the stent.

5. The inflatable stent of claim 1 further provided with a deployment rod for deploying the stent along a deployment path.

6. The inflatable stent of claim 5 wherein the deployment rod for deploying the stent passes through the passage and connects to the stent at an end of the stent.

7. The inflatable stent of claim 5 wherein the deployment rod includes an inflating tube for passage of an inflating fluid into the annular space.

8. The inflatable stent of claim 1 further provided with an inflating tube for passage of an inflating fluid into the annular space.

9. The inflatable stent of claim 1 provided with a sealing membrane to block flow through the passage or redirect flow through a side port or a selected end of the stent.

10. The inflatable stent of claim 1 wherein both the inner membrane and the outer membrane of the inflatable portion are generally cylindrical in form when inflated.

11. The inflatable stent of claim 1 wherein the connecting members are a plurality of membrane portions each extending from the inner membrane to the outer membrane.

12. The inflatable stent of claim 11 wherein the membrane portions run along substantially the whole length of the inner membrane.

13. The inflatable stent of claim 11 wherein the membrane portions divide the annular space into a series of axially extending cells around its circumference.

14. The inflatable stent of claim 13 wherein at least one end cap defines a circumferential space at an end of the stent that is in fluid communication with all of the cells or a selected cell or cells.

15. The inflatable stent of claim 13 wherein the plurality of membrane portions are made from a single sheet of flexible sheet material connecting alternately along the axial length of the inner membrane and then along the axial length of the outer membrane in a zig-zag arrangement to divide the annular space into cells.

16. The inflatable stent of claim 13 wherein the plurality of membrane portions are made from a single sheet of flexible sheet material bonding circumferentially along a portion of the inner membrane before extending radially to the outer membrane where it is bonded circumferentially along a portion before returning to the inner membrane, and so on to provide axially extending cells having a generally trapezoidal cross section.

17. The inflatable stent of claim 13 wherein the axially extending cells are all in fluid communication with each other.

18. The inflatable stent of claim 11 wherein the membrane portions extend outwards from the inner membrane to the outer membrane and run along the axial length of the stent.

19. The inflatable stent of claim 1 further comprising a second inflatable portion with a passage there through, wherein the inflatable portion and the second inflatable portion are connected to each other via a tubular portion of flexible sheet material, to provide flow through the stent as a whole.

20. A method of by-passing a section of pipe, the method comprising:
obtaining access to a section of pipe at two locations, one upstream and one downstream, to either side of a section of pipe to be by-passed;
deploying an inflatable stent into each of the two locations, the inflatable stent comprising an inflatable portion that comprises:
an inner membrane of a flexible sheet material defining a first end and a second end of the inflatable portion, and a passage there between when inflated; and
an outer membrane of a flexible sheet material disposed about the inner membrane, the outer membrane defining a first diameter of the stent when inflated;
wherein, when inflated, the inner and outer membranes are radially spaced apart to define an annular space there between;
the inner and outer membranes are connected by a plurality of connecting members in the annular space, and by first and second end caps that connect the membranes at the respective first and second ends of the inflatable portion;
wherein the inflatable portion is further provided with at least one inflatable pipe or lumen engaging portion that defines a second, larger diameter of the stent, when the inflatable portion is inflated; and
wherein the at least one inflatable pipe or lumen engaging portion is inflatable by being in fluid communication with the annular space and inflates when the annular space, or a part of the annular space, is inflated; and each inflatable stent having a passage therethrough;
inflating the stents so as to obtain substantially sealing engagement with the inner walls of the pipe;
providing a by-pass pipe running externally of the pipe from the upstream location to the downstream location; and
providing a route of fluid communication from upstream to downstream through the passages of the inflatable stents and via the by-pass pipe to by-pass the said section of pipe.

21. The method of claim 20 further wherein:
a third inflatable stent is provided and deployed through one of the access locations in the direction of the by-passed section of pipe, to allow venting and/or inspection of the by-passed section via a fluid communication.

22. An inflatable stent comprising an inflatable portion that comprises:
an inner membrane of a flexible sheet material defining a first end and a second end of the inflatable portion, and a passage there between when inflated; and
an outer membrane of a flexible sheet material disposed about the inner membrane, the outer membrane defining a first diameter of the stent when inflated;
wherein, when inflated, the inner and outer membranes are radially spaced apart to define an annular space there between;
the inner and outer membranes are connected by a plurality of connecting members in the annular space, and by first and second end caps that connect the membranes at the respective first and second ends of the inflatable portion;
wherein the inflatable portion is further provided with at least one inflatable pipe or lumen engaging portion that defines a second, larger diameter of the stent, when the inflatable portion is inflated;

wherein the at least one inflatable pipe or lumen engaging portion is inflatable by being in fluid communication with the annular space and inflates when the annular space, or a part of the annular space, is inflated; and further comprising a sealing membrane to block flow through the passage or redirect flow through a side port or a selected end of the stent.

23. The inflatable stent of claim 22 wherein the at least one inflatable pipe or lumen engaging portion is inflatable and is a larger diameter, when inflated, part of the outer membrane.

\* \* \* \* \*